(12) United States Patent
Simon et al.

(10) Patent No.: US 7,686,818 B2
(45) Date of Patent: Mar. 30, 2010

(54) LOCKING NAIL AND STEREOTAXIC APPARATUS THEREFOR

(75) Inventors: Bernd Simon, Kiel (DE); Rene Füllgraf, Achterwehr (DE)

(73) Assignee: Stryker Trauma GmbH (DE)

( * ) Notice: Subject to any disclaimer, the term of this patent is extended or adjusted under 35 U.S.C. 154(b) by 1299 days.

(21) Appl. No.: 10/946,538

(22) Filed: Sep. 21, 2004

(65) Prior Publication Data
US 2005/0080335 A1    Apr. 14, 2005

(30) Foreign Application Priority Data
Sep. 24, 2003    (DE)    ............... 203 14 742 U

(51) Int. Cl.
*A61B 17/72* (2006.01)
(52) U.S. Cl. ...................... 606/130; 600/424
(58) Field of Classification Search ............ 606/53, 606/60, 62, 64, 67, 86 R, 96, 98, 104, 130; 600/424
See application file for complete search history.

(56) References Cited

U.S. PATENT DOCUMENTS

| | | | |
|---|---|---|---|
| 3,757,209 A * | 9/1973 | Schonstedt | 324/245 |
| 4,621,628 A | 11/1986 | Brudermann | |
| 4,622,644 A | 11/1986 | Hansen | |
| 4,849,692 A | 7/1989 | Blood | |
| 4,945,305 A | 7/1990 | Blood | |
| 5,049,151 A * | 9/1991 | Durham et al. | 606/98 |
| 5,127,913 A | 7/1992 | Thomas, Jr. | |
| 5,251,127 A | 10/1993 | Raab | |
| 5,305,203 A | 4/1994 | Raab et al. | |
| 5,411,503 A * | 5/1995 | Hollstien et al. | 606/86 R |
| 5,417,688 A | 5/1995 | Elstrom et al. | |
| 5,426,687 A | 6/1995 | Goodall et al. | |
| 5,433,720 A | 7/1995 | Faccioli et al. | |
| 5,453,686 A | 9/1995 | Anderson | |
| 5,478,343 A | 12/1995 | Ritter et al. | |

(Continued)

FOREIGN PATENT DOCUMENTS

DE        196 40 474        4/1998

(Continued)

*Primary Examiner*—Eduardo C Robert
*Assistant Examiner*—Tara R George
(74) *Attorney, Agent, or Firm*—Lerner, David, Littenberg, Krumholz & Mentlik, LLP

(57) ABSTRACT

A stereotaxic apparatus for a locking nail which has two oscillating circuits which are disposed along the longitudinal direction of the locking nail. The apparatus has a guide sleeve to place a drill and/or bone screw which, when the stereotaxic apparatus is in an oriented condition, points to a cross-bore in the locking nail. The guide sleeve has three or more oscillating circuits arranged in a first plane that are equidistant each from a first center located in the plane; three or more oscillating circuits are arranged in a second plane extending in parallel with said first plane that are equidistant each from a second center located in said second plane. The first and second planes are arranged towards each other such that a face normal to one of said planes extends through the first and second centers. A pair of oscillating circuits are arranged at a distance from a straight line extending through the centers and the interconnecting straight line of which, in the aligned condition with the locking nail, is substantially perpendicular to the longitudinal direction of the locking nail.

22 Claims, 2 Drawing Sheets

U.S. PATENT DOCUMENTS

| | | | |
|---|---|---|---|
| 5,514,145 A * | 5/1996 | Durham et al. | ............... 606/96 |
| 5,517,990 A | 5/1996 | Kalfas et al. | |
| 5,540,691 A | 7/1996 | Elstrom et al. | |
| 5,584,838 A * | 12/1996 | Rona et al. | .................... 606/96 |
| 5,707,375 A | 1/1998 | Durham et al. | |
| 5,748,767 A | 5/1998 | Raab | |
| 5,772,594 A | 6/1998 | Barrick | |
| 6,036,696 A | 3/2000 | Lambrecht et al. | |
| 6,074,394 A | 6/2000 | Krause | |
| 6,162,228 A | 12/2000 | Durham | |
| 6,185,452 B1 | 2/2001 | Schulman et al. | |
| 6,208,894 B1 | 3/2001 | Schulman et al. | |
| 6,340,363 B1 | 1/2002 | Bolger et al. | |
| 6,370,418 B1 | 4/2002 | Bernoski et al. | |
| 6,470,207 B1 | 10/2002 | Simon et al. | |
| 6,503,249 B1 | 1/2003 | Krause | |
| 6,520,969 B2 | 2/2003 | Lambrecht et al. | |
| 6,616,670 B2 | 9/2003 | Simon et al. | |
| 6,654,629 B2 | 11/2003 | Montegrande | |
| 6,697,664 B2 | 2/2004 | Kienzle III et al. | |
| 6,892,090 B2 | 5/2005 | Verard et al. | |
| 7,001,346 B2 | 2/2006 | White | |
| 7,060,075 B2 * | 6/2006 | Govari et al. | ................. 606/98 |
| 2001/0001125 A1 | 5/2001 | Schulman et al. | |
| 2002/0052604 A1 * | 5/2002 | Simon et al. | .................. 606/62 |
| 2004/0011365 A1 | 1/2004 | Govari et al. | |
| 2004/0034355 A1 | 2/2004 | Govari et al. | |
| 2004/0097952 A1 | 5/2004 | Sarin et al. | |
| 2004/0181149 A1 | 9/2004 | Langlotz et al. | |
| 2005/0075562 A1 | 4/2005 | Szakelyhidi et al. | |
| 2005/0080335 A1 | 4/2005 | Simon et al. | |
| 2005/0080427 A1 | 4/2005 | Govari et al. | |
| 2006/0084867 A1 | 4/2006 | Tremblay et al. | |
| 2006/0173291 A1 | 8/2006 | Glossop | |
| 2007/0016008 A1 | 1/2007 | Schoenefeld | |
| 2007/0016009 A1 | 1/2007 | Lakin et al. | |

FOREIGN PATENT DOCUMENTS

| | | |
|---|---|---|
| WO | WO-9302626 | 2/1993 |
| WO | WO-9713467 | 4/1997 |
| WO | WO-2006103071 | 10/2006 |

* cited by examiner

LOCKING NAIL AND STEREOTAXIC APPARATUS THEREFOR

BACKGROUND OF THE INVENTION

The present invention relates to a stereotaxic apparatus for a locking nail which has two oscillating circuits arranged along its longitudinal direction. The invention also relates to the locking nail.

Locking nails which can be introduced in the shin and thigh bones mostly have several cross-bores through which bone screws are passed to hold the locking nail safely in the bone channel. A particular difficulty in doing so is to locate the cross-bore in the implanted nail. The purpose is served by stereotaxic apparatus. In a category of stereotaxic apparatus, the bone is radiographed by X-rays and the cross-bores of the locking nail in the bone are visualized on a monitor. Additionally, a target element is illustrated in the X-ray image so that a marking lying on the axis of the cross-bore can be made at the outside of the bone.

In another category of stereotaxic apparatus, the apparatus is fixedly joined to the implantable nail. A bracket-like portion has at least one bore which has its axis aligned with the axis of the cross-bore of the nail when the stereotaxic apparatus has been mounted. For a guidance of the drilling tool or bone screw, it is also known to put a guide sleeve through the bore of the stereotaxic apparatus that is advanced up to the outside of the bone.

SUMMARY OF THE INVENTION

U.S. Pat. No. 5,411,503 relates to a target instrument for locking nails in medullary bones. In the method, a pointed bar is introduced into the hollow shank of the locking nail. The pointed bar is provided with two oscillating circuits at its distal end. The pointed bar has a stop at its proximal end. To position the pointed bar, it is completely inserted into the locking nail which has been driven in to a long bone, with the stop element abutting at the free end of the locking nail. The two oscillating circuits at the end of the pointed bar are excited and the electromagnetic field emitted is detected by appropriate sensors in the stereotaxic apparatus. The stereotaxic apparatus is oriented in the field of the oscillating circuits in such a way that a guide channel for the drill that is connected thereto becomes oriented in accordance with the axis of the cross-bore on the bone nail. The drawback of this device is that it is impossible to take into account any warp or distortion of the locking nail that occurs while it is being driven in.

U.S. Pat. No. 5,584,838, the disclosure of which is incorporated herein by reference, relates to a bone nail the hollow shank of which has inserted therein an element with a single oscillating circuit. The nail is driven into the bone with its element inserted so that the above described drawbacks cannot appear if the nail is warped. However, a drawback of a locking nail configured in this way is that since only a single oscillating circuit is used a comparatively expensive stereotaxic apparatus is required to orient the drill. Further, it proves a disadvantage that the oscillating circuit is arranged just in the channel of the cross-bore and has to be removed after the stereotaxic apparatus is oriented.

U.S. Pat. No. 5,584,838 also relates to a stereotaxic apparatus for the axial orientation of a guide sleeve in which the guide sleeves are provided with two couples of measuring coils which detect magnet field of a coil disposed in the nail and aligned with the cross-bore. For an orientation, the stereotaxic apparatus is positioned so as to cause each couple of the two coils to receive a magnetic field of an equal intensity.

U.S. Pat. No. 4,621,628 relates to a further device for discovering cross-bores in intramedullary implants. It involves an orientation of a magnetic field in the cross-bore and a measurement of the axis of the cross-bore from outside by means of a magnetic field measuring device.

U.S. Pat. No. 6,616,670 relates to a bone nail bore targeting system which includes signal generators located at pre-determined distances from the cross-bores.

It is one aspect of the present invention to provide a stereotaxic apparatus for a locking nail which allows detection of the position of the cross-bore in the locking nail as exactly and reliably as possible by simple means.

The inventive stereotaxic apparatus is designed to orient a guide sleeve to place a drill and/or bone screw relative to a cross-bore of an inserted locking nail. For this purpose, the locking nail has two oscillating circuits which are arranged along the longitudinal direction of the locking nail. When the stereotaxic apparatus is in an oriented condition the central axis of the guide sleeve essentially coincides with the central axis of the cross-bore. The stereotaxic apparatus has three or more oscillating circuits in a first plane that are equidistant each from a first center located in said plane. Three or more oscillating circuits are also arranged in a second plane extending in parallel with said first plane and are equidistant each from a second center located in said second plane. The first and second planes are arranged towards each other such that a face normal to one of the planes extends through the first and second centers. Additionally, a pair of oscillating circuits are provided spaced from the straight line extending through said centers, the interconnecting straight line of the oscillating circuits, in the condition aligned with the locking nail of the stereotaxic apparatus, is substantially perpendicular to the longitudinal direction of the locking nail. The first plane serves from positioning in an xy plane. For a better survey, the axis of the cross-bore extends in a z direction, and the longitudinal direction of the locking nail in the x direction. Needless to say that the inventive stereotaxic apparatus can also be employed if the longitudinal direction of the locking nail and the axis of the cross-bore are not orthogonal to each other. With this geometry, the first plane including the oscillating circuits defines the position of the stereotaxic apparatus in the xy plane. To discover the correct position, a search is made of that position of the stereotaxic apparatus in which the oscillating circuits in the first plane receive an electromagnetic field of an oscillating circuit in the locking nail at the same intensity. Once the position is fixed in the xy plane it has to be made sure that the axis of the guide sleeve or stereotaxic apparatus is prevented from tilting with respect to the z axis of the cross-bore. The purpose is served by the second plane arranged in parallel with the first plane with its oscillating circuits. If signals of the same intensity are also detected by these oscillating circuits it is sure that the axes of the guide sleeve and cross-bore coincide. However, it is still possible to rotate the stereotaxic apparatus about this axis. To fix this degree of freedom as well, the additional pair of oscillating circuits helps in measuring the signal of a second oscillating circuit from the locking nail. To this end, the additional pair of oscillating circuits is oriented to be perpendicular to the longitudinal direction of the locking nail. If the two oscillating circuits receive signals of an equal intensity the stereotaxic apparatus has been oriented completely in a precisely defined position to the bone nail and the position of the cross-bores can be determined relative to this reference position. The oscillating circuits provided in the locking nail and stereotaxic apparatus are preferably operated at their resonant frequency.

In a preferred aspect, four oscillating circuits are arranged in a rectangle towards each other in the first and/or second plane. It is preferred to choose a square as the rectangle. The rectangular arrangement of the receiving oscillating circuits in the planes of the stereotaxic apparatus appreciably increases the accuracy in positioning.

In a preferred aspect, the oscillating circuits are arranged in congruence in the first and second planes. This means that if the planes extending in parallel with each other are caused to be congruent along their normal faces the oscillating circuits are disposed on top of each other in the planes.

In a possible aspect of the inventive stereotaxic apparatus, the signals received from the oscillating circuits can be routed on to an external or internal evaluation unit. For a display of the corrected position, it is possible for the position to be shown on the stereotaxic apparatus itself or on an external display or on both of them.

The evaluation unit has filtration and amplification units which are turned to a work frequency of the oscillating circuits. The amplification unit preferably has an amplifier and a bandpass filter with such amplification substantially taking place by an active bandpass filter.

The amplified and filtered measuring values are rectified and are digitized via an A/D converter. The digitized data can be routed, via a serial interface, on to a computer (PC) for an evaluation. The PC represents the additionally or exclusively evaluated data in order to display the oriented condition of the stereotaxic apparatus and possibly the direction and/or the amount of deviation from the oriented position.

To enable the receiving oscillating circuits to receive an electromagnetic signal and oscillate accordingly, it is necessary for the oscillating circuits to be excited in the locking nail. For an excitation of these oscillating circuits, it is preferred to provide an excitation coil in the stereotaxic apparatus that emits a high-frequency pulse into the locking nail to excite the oscillating circuits.

The inventive locking nail has a hollow shank which has at least one cross-bore to receive a bone screw and an elongate recess in the area of the at least one cross-bore. The recess which preferably is boat-shaped has arranged therein two oscillating circuits of different emission frequencies in the longitudinal direction of the shank. The oscillating circuits are oriented within the recess in such a way that the directions of emissions of the electromagnetic fields extend in parallel with each other.

The recess is provided in the shank wall from outside to facilitate the assembly of the oscillating circuits in the locking nail. Once the oscillating circuits are inserted the recess is closed with a plastic.

According to a preferred aspect, at least one of the oscillating circuits is arranged around a cross-bore.

These and other aspect of the invention are provided by a system for locating a bore in a medical implant wherein the implant includes an oscillating circuit located in a known spatial relationship to the bore. A guide sleeve, such as a drill guide sleeve, has at least three oscillating circuits attached thereto located on a first plane and at least three oscillating circuits attached thereto located in a second plane oriented parallel to and spaced from the first plane along an axis. The guide sleeve includes a pair of oscillating circuits spaced on opposite sides of an axis extending perpendicularly from the axis along which the two planes are spaced. A stereotactic sensing system is provided for sensing the relative locations of each of the oscillating circuits and their relative intensities such that when corresponding oscillating circuit intensities are equal, the axial alignment of the guide sleeve with the bore in the locking nail can be confirmed.

The preferred locking nail comprises a hollow shank which has at least one cross-bore for the reception of the bone screw and a preferably elongate recess arranged in the area of the at least one cross-bore. The recess includes two oscillating circuits having different resident frequencies arranged in the series. The circuits are oriented in the recess such that the primary direction of radiation of the electromagnetic fields produced by the oscillating circuits extend in parallel to each other. The recess may be sealed by a biocompatible plastic compound. The oscillating circuits can be arranged in a recess surrounding the at least one cross-bore.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
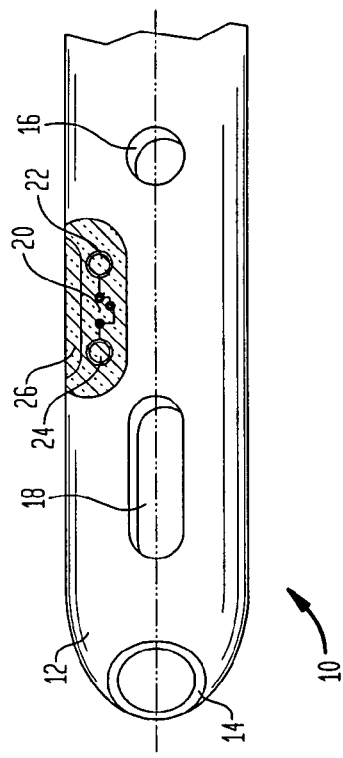
FIG. 1 shows the tip of a locking nail including two oscillating circuits.

FIG. 1 shows the top of a preferred locking nail 10 which has a hollow or cannulated shank 12 with an opening in the tip 14. Two cross-bores 16 and 18 are provided in the shank 12. The cross-bore 18 is designed as an elongate hole in the embodiment shown. In the shank wall, a recess 20 is countersunk into the shank wall in the area between the cross-bores 16 and 18. Two schematically shown oscillating circuits 22 and 24 are provided in the recess 20. The oscillating circuits have a coil and a capacitor each of which are electrically tuned to each other. In the embodiment shown, the oscillating circuits are interconnected electrically. However, it is also imaginable to provide two electrically independent oscillating circuits. For an excitation of the oscillating circuits, the stereotaxic apparatus generates a short high-frequency pulse (HF pulse). The frequency of the pulse corresponds to the resonant frequency of the oscillating circuit requiring excitation in the nail or is in a close vicinity of the resonant frequency so that no large attenuation will occur in the oscillating circuit. The HF field generated excites the respective oscillating circuit in the nail. After the HF excitation field is turned off the energy stored in the oscillating circuit causes the oscillating circuit to continue oscillating for a period of some milliseconds while generating a decaying HF field itself. This field is received by the stereotaxic apparatus in its oscillating circuits and is analyzed. The HF pulse is generated by a large-surface coil in the stereotaxic apparatus. The exciting field has a uniform field intensity distribution across the entire target area to achieve a constantly strong excitation of the oscillating circuits in the nail regardless of the position of the nail in the coverage area. Thus, the excitation of the oscillating circuits in the nail takes place via a HF pulse in a wireless manner unlike the one in U.S. Publication No. 2004/0010252. This kind of excitation makes it possible to employ the oscillating circuits provided in the nail both as reception and transmission oscillating circuits.

The oscillating circuits provided in the recess 20 are electrically insulated by an appropriate biocompatible plastic 26. It goes without saying that the coils are also insulated from the wall of the shank.

Figure 2:
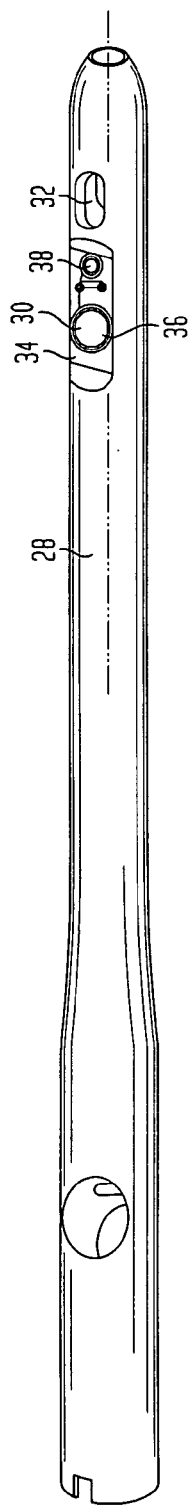
FIG. 2 shows a locking nail including two oscillating circuits one of which extends around one of the cross-bores.

FIG. 2 shows an alternative aspect of the inventive locking nail. In this embodiment, the locking nail 28 has two cross-bores 30 and 32 in the areas of its tip. The cross-bore 32 is again configured as an elongate hole. Unlike in the embodiment of FIG. 1, the recess for the two oscillating circuits are not disposed between the bores, but around the cross-bore 30. Two oscillating circuits 36, 38 are provided in the recess 34 with the oscillating circuits 36 running around the cross-bore 30.

Figure 3:
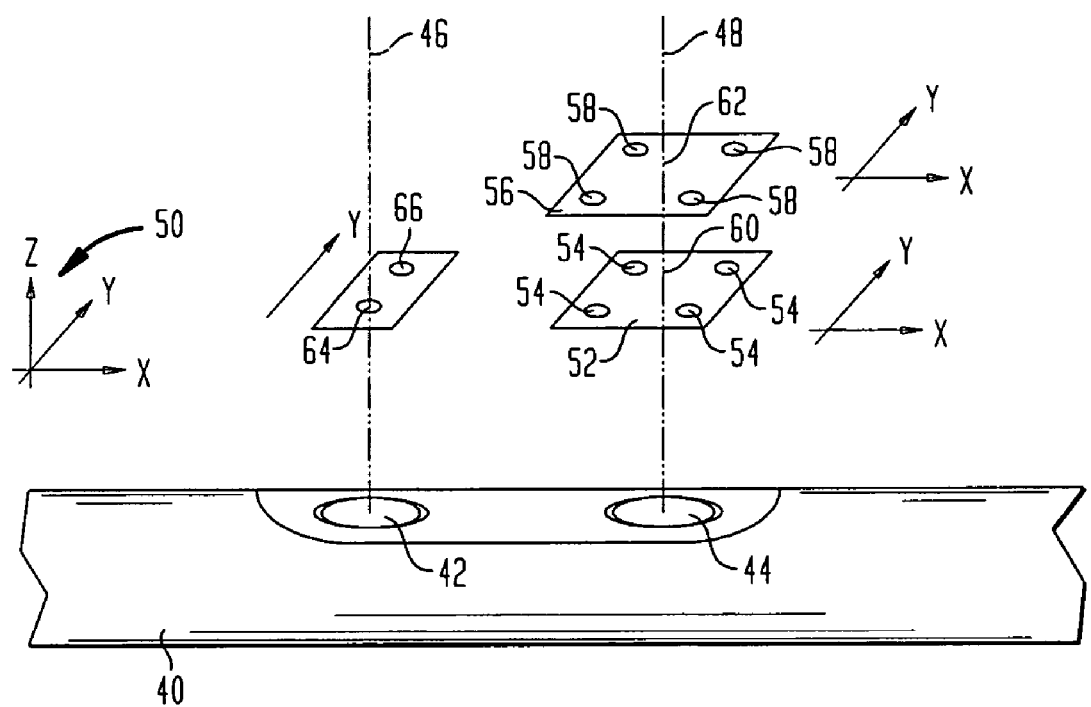
FIG. 3 shows the orientation of the seat of the oscillating circuits relative to the oscillating circuits within the locking nail.

FIG. 3 shows a schematic sketch of a locking nail 40 with two oscillating circuits 42, 44. The coils of the oscillating circuits 42, 44 are arranged in the shank wall in such a way that their main emission axes 46, 48 extend in parallel with each other. Further, the coils 42 and 44 are disposed along the longitudinal axis of the locking nail. For more ease of orientation, a coordinate system 50 is shown in which the x axis runs along the longitudinal axis of the locking nail and the z axis runs along the direction of main emission 46 and 48. Four oscillating circuits 54 are arranged at a square in a first plane 52. The first plane extends in the xy plane as referred to the coordinate system 50 shown in the drawings. In parallel with the first plane, a second plane 56 is provided in which four oscillating circuits 58 are also arranged at a square. The planes 52 and 56 are arranged in parallel with each other and the oscillating circuits are located on top of each other as referred to the z direction. The midpoint of the square in the first plane 52 is designated 60 whereas the midpoint of the square in the second plane 56 is designated 62. Although the oscillating circuits of the embodiment are shown in congruence on top of each other such an arrangement is not necessary. The oscillating circuits may also be disposed as offset from each other.

FIG. 3 shows the oriented position of the first plane 52 and the second plane 56 in which the main axis of emission 48 breaks through the centers 60 and 62.

If all of the four reception oscillating circuits 54 in the first plane measure an equally strong signal the stereotaxic apparatus has been oriented in the xy plane. To prevent it from tilting, it is indispensable that the oscillating circuits 58 also supply equally strong signals. This condition ensures that both the xy plane has been hit and it is prevented from tilting. A rotation of the stereotaxic apparatus about the axis 48 remains as a degree of freedom. An additional couple of reception oscillating circuits 64, 66 is provided to locate the stereotaxic apparatus also with respect to this degree of freedom. The coils 64 and 66 are aligned along the direction indicated by "y" and extend in the xy direction each. If the coils 64, 66 also show equally strong signals the orientation of the stereotaxic apparatus has been located with respect to the axis 48 and a guide sleeve (not shown) faces the direction of one of the cross-bores.

The evaluation electronics includes two filtration and amplification units which are tuned each to the working frequency of a transmission coil in the locking nail. The coil unit is coupled thereto via a 2×8 multiplexer module. The multiplexer is controlled by a microcontroller which determines which measuring coil to connect to the amplification unit. The amplification unit comprises an amplifier and a bandpass filter. For an improvement to malfunction immunity, most of the amplification is performed by a specifically dimensioned active bandpass filter. After this amplification and filtration, the signal is rectified and routed on to an A/D converter. The A/D converter, preferably of 12 bits, is controlled by the microcontroller, as is the multiplexer. The converted data is then transferred to a PC via a serial link by means of the microcontroller. The PC evaluates the data and graphically displays the location of the stereotaxic apparatus relative to the cross-bores of the locking nail.

As was already mentioned, the coils 42 and 44 are excited via an excitation coil (not shown) in the stereotaxic apparatus. The excitation coil is arranged here such as to prevent the HF pulse from interfering with the reception coils 54, 58, 64 and 66.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stereotaxic apparatus for a locking nail comprising two oscillating circuits which are disposed in a recess in an outer surface of the nail along the longitudinal direction of the locking nail and spaced from a cross-bore in the nail, the apparatus having a guide sleeve to place a drill or bone screw which, when the stereotaxic apparatus is in an oriented condition, points to a cross-bore in the locking nail wherein the stereotactic apparatus has:

three or more oscillating circuits are arranged in a first plane that are equidistant each from a first center located in said plane;

three or more oscillating circuits are arranged in a second plane extending in parallel with said first plane that are equidistant each from a second center located in said second plane;

wherein said first and second planes are arranged towards each other such that a face normal to one of the planes extends through said first and second centers; and at least two oscillating circuits are arranged at a distance from a straight line extending through said centers and the interconnecting straight line of which, in the condition aligned with said locking nail, is substantially perpendicular to the longitudinal direction of said locking nail wherein an additional excitation coil is provided which emits a HF pulse for an excitation of the oscillating circuits in the locking nail.

2. The stereotaxic apparatus as set forth in claim 1 wherein four oscillating circuits are arranged at a rectangle towards each other in said first plane.

3. The stereotaxic apparatus as set forth in claim 2 wherein said oscillating circuits are arranged at a square towards each other.

4. The stereotaxic apparatus as set forth in claim 1 wherein said oscillating circuits are arranged as a rectangle in said second plane.

5. The stereotaxic apparatus as set forth in claim 4 wherein said oscillating circuits are arranged at a square towards each other.

6. The stereotaxic apparatus as set forth in claim 1 wherein said oscillating circuits are arranged in congruence in said first and second planes.

7. The stereotaxic apparatus as set forth in claim 1 wherein said oscillating circuits are connected to an internal evaluation unit.

8. The stereotaxic apparatus as set forth in claim 7 wherein said evaluation unit has filtration and amplification units which are each tuned to a working frequency of said oscillating circuits.

9. The stereotaxic apparatus as set forth in claim 8 wherein said amplification unit has an amplifier and a bandpass filter with amplification substantially taking place by an active bandpass filter.

10. The stereotaxic apparatus as set forth in claim 9 wherein the amplified and filtered measuring values of the oscillating circuits are rectified and are digitized via an A/D converter.

11. The stereotaxic apparatus as set forth in claim 10 wherein the digitized data is routed, via a serial interface, onto a computer for an evaluation.

12. The stereotaxic apparatus as set forth in claim 11 wherein the evaluated data are graphically plotted on the computer.

13. The stereotaxic apparatus as set forth in claim 1 wherein said oscillating circuits are connected to an external evaluation unit.

14. The stereotaxic apparatus as set forth in claim 13 wherein said evaluation unit has filtration and amplification units which are each tuned to a working frequency of said oscillating circuits.

15. The stereotaxic apparatus as set forth in claim 14 wherein said amplification unit has an amplifier and a bandpass filter with amplification substantially taking place by an active bandpass filter.

16. The stereotaxic apparatus as set forth in claim 15 wherein the amplified and filtered measuring values of the oscillating circuits are rectified and are digitized via an A/D converter.

17. The stereotaxic apparatus as set forth in claim 16 wherein the digitized data is routed, via a serial interface, onto a computer for an evaluation.

18. The stereotaxic apparatus as set forth in claim 17 wherein the evaluated data are graphically plotted on the computer.

19. A locking nail comprising a hollow shank having an outer bone contacting surface which has at least one crossbore for the reception of a bone screw and a recess in the outer bone contacting surface of the bone nail shank the recess having an outwardly facing surface located radially closer to a central longitudinal axis of the nail than the outer bone contact surface, the recess spaced from the at least one crossbore, two oscillating circuits having different resonant frequencies are mounted in the recess outwardly of the outermost surface thereof, the two oscillating circuits electrically connected in the recess in series, the oscillating circuits being oriented in said recess along parallel axis such that the main direction of radiation of the electromagnetic fields produced extend in parallel to each other, the oscillating circuits responding to a HF pulse into the locking nail by producing the parallel electromagnetic fields.

20. The locking nail as set forth in claim 19 wherein said recess is sealed by a plastic compound.

21. The locking nail as set forth in claim 20 wherein at least one of said oscillating circuits is arranged around a crossbore.

22. The locking nail as set forth in claim 19 wherein said oscillating circuits are operated by their resonant frequency.

* * * * *